United States Patent [19]

Fischell et al.

[11] Patent Number: 5,492,530
[45] Date of Patent: Feb. 20, 1996

[54] METHOD FOR ACCESSING THE CORONARY ARTERIES FROM THE RADIAL OR BRACHIAL ARTERY IN THE ARM

[75] Inventors: Robert E. Fischell, Dayton, Md.; David R. Fischell, Fair Haven, N.J.; Tim A. Fischell, Nashville, Tenn.

[73] Assignee: Cathco, Inc., Dayton, Md.

[21] Appl. No.: 384,277

[22] Filed: Feb. 2, 1995

Related U.S. Application Data

[63] Continuation-in-part of Ser. No. 192,347, Feb. 7, 1994, Pat. No. 5,389,090.
[51] Int. Cl.⁶ ............................................. A61M 31/00
[52] U.S. Cl. ............................................. 604/49; 604/280
[58] Field of Search .................. 604/49, 50–52, 604/280–283, 95, 264; 606/191, 192, 194

[56] References Cited

U.S. PATENT DOCUMENTS

| | | | |
|---|---|---|---|
| 5,053,007 | 10/1991 | Euteneuer | 606/194 |
| 5,129,887 | 7/1992 | Euteneuer et al. | 604/283 X |
| 5,224,939 | 7/1993 | Holman et al. | 604/283 |
| 5,389,090 | 2/1995 | Fischell et al. | 604/280 |
| 5,401,258 | 3/1995 | Voda | 604/280 X |
| 5,445,625 | 8/1995 | Voda | 604/281 |

Primary Examiner—John D. Yasko

[57] ABSTRACT

The present invention is a method for using an improved guiding catheter that eliminates the need for an introducer sheath or a separate Tuohy-Borst "Y" adaptor, thus reducing the time and expense for performing artery opening procedures. Furthermore, the guiding catheter with straightening dilator as described herein allows the hole in the wall of the femoral artery in the groin, or even more advantageously, the radial artery in the arm to be approximately 2 French sizes smaller in diameter as compared to the hole that would be created if an introducer sheath is also used. The advantages of the present invention are accomplished by utilizing a guiding catheter with a dilator that has a stiffened and/or curved distal section that can be used to straighten the distal section of the guiding catheter as it is advanced through the arterial system. The guiding catheter plus dilator can then be used in a manner similar to an introducer sheath to percutaneously enter the artery by being advanced over a previously placed guide wire. Once the distal ends of the dilator and the guiding catheter are placed near the ostium of the coronary artery, the dilator and guide wire are withdrawn which allows the guiding catheter to assume its normal bent shape (e.g., a Judkin's bend) near its distal end. The cardiologist can then, by well known techniques, place the guiding catheter's distal end in the ostium of a coronary artery. Any of several well known procedures can then be performed including angiography, balloon angioplasty, atherectomy or stent placement.

19 Claims, 3 Drawing Sheets

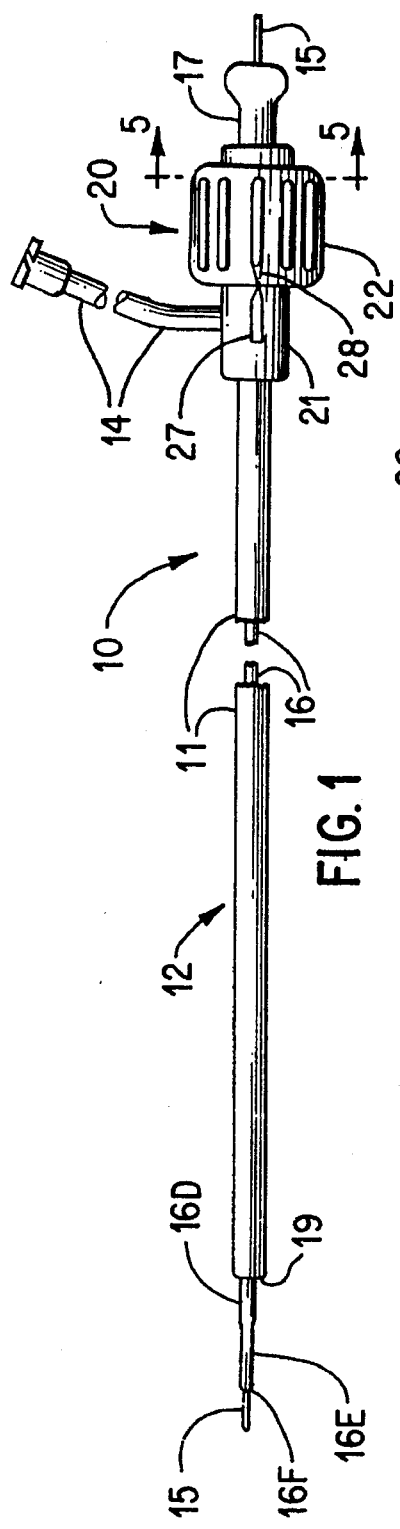
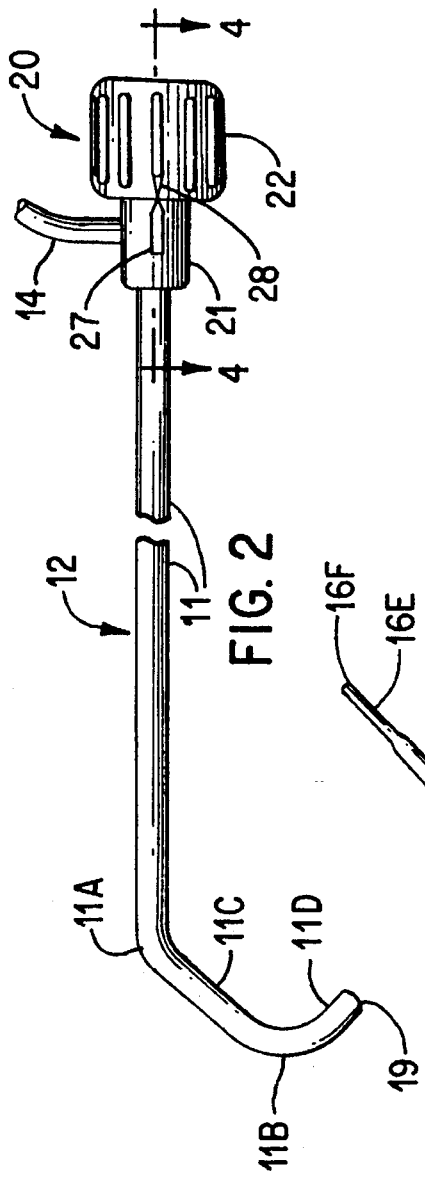
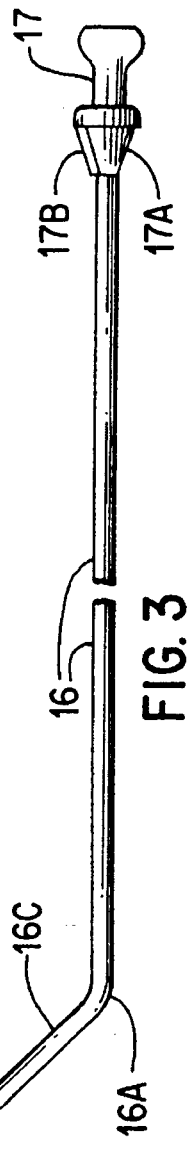

5,492,530

METHOD FOR ACCESSING THE CORONARY ARTERIES FROM THE RADIAL OR BRACHIAL ARTERY IN THE ARM

This is a continuation in-part application of Ser. No. 08/192,347 filed Feb. 7, 1994 now U.S. Pat. No. 5,389,090.

FIELD OF USE

This invention is in the field of guiding catheters for introducing guide wires and artery opening catheters into the arterial system of human beings and specifically, this is an improved method for accessing the coronary arteries by means of the radial or brachial artery in the arm.

BACKGROUND OF THE INVENTION

To access the coronary (or other) arteries for a variety of purposes including dilation of stenoses, an interventional cardiologist would first introducer a guide wire through an arterial access needle puncture at the groin, and then an introducer sheath with dilator would be advanced over the guide wire and into the lumen of the femoral artery. The dilator would then be removed and a guiding catheter would be advanced through the sheath and over the guide wire until the guiding catheter's distal end would be situated in the ostium of a coronary artery. An artery opening catheter (such as a balloon angioplasty catheter or atherectomy catheter) would then be advanced through the guiding catheter, and an angioplasty or atherectomy procedure would be performed to open an arterial stenosis. In recent practice, intra-arterial stents are placed at the site of the opened stenosis by means of a stent delivery catheter. These stent delivery catheters require a fairly large diameter guiding catheter; typically 9 or 10 French size. Since the outer diameter of the sheath through which the guiding catheter is inserted is typically 2 French sizes larger then the size of the guiding catheter, a fairly large diameter hole must be made through the wall of the femoral artery. These larger size holes often lead to excessive bleeding at the groin after the sheath is removed. Furthermore, the radial artery from the arm could be used for accessing coronary arteries, but it is even more sensitive to the diameter of catheters passing through it as compared to the femoral artery at the groin.

To perform an artery opening procedure with a guiding catheter, it is also necessary to attach a Tuohy-Borst "Y" adaptor onto the guiding catheter's proximal end. The introducer sheath and Tuohy-Borst "Y" adaptor are each components that require additional time for the interventional cardiologist to properly place, and they add to the cost of performing artery opening procedures.

SUMMARY OF THE PRESENT INVENTION

The present invention is a method for using an improved guiding catheter that eliminates the need for an introducer sheath or a separate Tuohy-Borst "Y" adaptor, thus reducing the time and expense for performing artery opening procedures. Furthermore, the guiding catheter with straightening dilator as described herein allows the hole in the wall of the femoral artery in the groin, or even more advantageously, the radial or brachial artery in the arm to be approximately 2 French sizes smaller in diameter as compared to the hole that would be created if an introducer sheath is also used.

The advantages of the present invention are accomplished by utilizing a guiding catheter with a dilator that has a stiffened and/or curved distal section that can be used to straighten the distal section of the guiding catheter as it is advanced through the arterial system. The guiding catheter plus dilator can then be used in a manner similar to an introducer sheath to percutaneously enter artery by being advanced over a previously placed guide wire. Once the distal ends of the dilator and guiding catheter are placed near the ostium of the coronary artery, the dilator and guide wire are withdrawn which allows the guiding catheter to assume its normally bent shape (e.g., a Judkin's bend) near its distal end. The cardiologist can then, by well known techniques, place the guiding catheter's distal end in the ostium of a coronary artery. Any of several well known procedures can then be performed including angiography, balloon angioplasty, atherectomy or stent placement.

Although the method described herein could be used with a conventional guiding catheter design, the guiding catheter of the present invention might also utilize the unique feature of an integrally formed Tuohy-Borst fitting with a side arm at the guiding catheter's proximal end. This capability obviates the need for attaching a separate Tuohy-Borst fitting at the guiding catheter's proximal end to accomplish the same functions of arterial access with minimum bleeding. The guiding catheter's Tuohy-Borst fitting could be tightened around guide wires or the shaft of catheters that are advanced through the guiding catheter. The side arm would typically terminate in a female Luer fitting that can be attached to a manifold for the introduction of saline solution, contrast medium or medications. Thus, the Tuohy-Borst fitting with side arm at the guiding catheter's proximal end eliminates the need for a separate Tuohy-Borst fitting.

Thus, it is an objective of the present invention to have a method that allows placement of a guiding catheter without requiring insertion of the guiding catheter through an introducer sheath thus allowing a smaller hole to be made in the wall of the femoral, radial or brachial artery.

Still another objective of the invention is to utilize a dilator having a curved distal section that when placed inside a guiding catheter causes the dilator-guiding catheter assembly to be essentially straight for easy insertion through the arterial system.

Still another objective of the invention is to use a straightening dilator of increased stiffness so that it straightens the distal section of a guiding catheter which guiding catheter also has increased stiffness at its distal section so that when the dilator is withdrawn, the distal section of the guiding catheter will more strongly maintain its placement in the ostium of a coronary artery.

Still another objective of the invention is to reduce the cost and time required for performing arterial interventional procedures.

Still another objective of the invention is to allow earlier discharge of the patient by arterial access through the radial or brachial artery as compared to the femoral artery.

Still another objective of the invention is to eliminate excessive bleeding through the guiding catheter when it is being inserted.

These and other objects and advantages of this invention will become obvious to a person of ordinary skill in this art upon reading of the detailed description of this invention including the associated drawings.

BRIEF DESCRIPTION OF THE DRAWINGS

FIG. 1 is a side view of a guiding catheter system including a guide wire, straightening dilator and a guiding catheter with Tuohy-Borst fitting.

FIG. 2 is a side view of a guiding catheter with Tuohy-Borst fitting at its proximal end.

FIG. 3 is a side view of a straightening dilator.

DETAILED DESCRIPTION OF THE INVENTION

Figure 4:
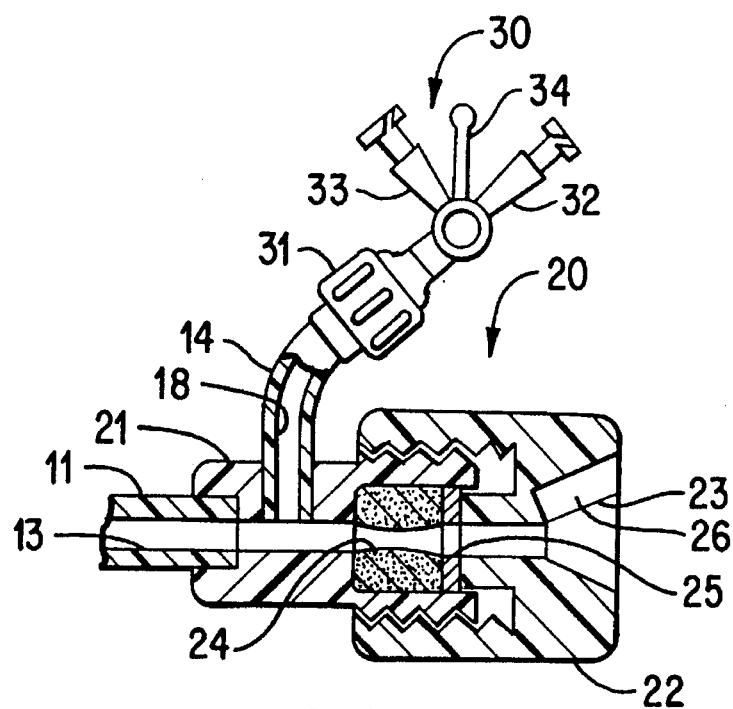
FIG. 4 is an enlarged, partial longitudinal cross section of the proximal end of the guiding catheter at section 4—4 of FIG. 2.

FIGS. 1, 2 and 3 illustrate the guiding catheter system 10 having a guiding catheter 12 with an elongated tube 11 with a tapered distal end 19, and a Tuohy-Borst fitting 20, a guide wire 15 and a straightening dilator 16. The dilator 16 (particularly as shown in FIG. 3) has a distal section with a first bend 16A and a second bend 16B, and a first distal section 16C, a second section 16D, and a third section 16E that is aligned with section 16D but of smaller diameter. The section 16E has a tapered distal end 16F designed to fit snugly around a guide wire as that distal end 16F is advanced through the arterial system. It should be understood that there could be only one bend, or more than two bends at this distal section of the dilator. All the sections 16 of the dilator are designed to fit slideably within the interior lumen of the guiding catheter tube 11. The dilator also has at its proximal end a handle 17 with a cone 17A having a key 17B for mating with the threaded nut 22 of the Tuohy-Borst fitting 20 as seen in FIG. 5.

As seen in FIG. 2, the guiding catheter tube 11 has bends 11A and 11B along a distal section, and furthermore has distal sections 11C and 11D. The guiding catheter 12 also has a Tuohy-Borst fitting 20 at its proximal end. As seen in FIGS. 1, 2 and 4, the Tuohy-Borst fitting 20 is integrally attached as a one-piece construction with the tube 12 and has a threaded base 21, a side arm 14 having a female Luer lock fitting, a threaded nut 22 with conical entry lumen 23, a soft elastomer gland 24 and a comparatively hard washer 25. When the nut 22 is not tightened down, the gland 24 is not compressed and the lumen 23 is in fluid communication with the lumen 13 of the elongated tube 11 and the lumen 18 of the side arm 14. When the nut 22 is screwed into the threaded base 21, the washer 25 compresses the soft elastomer gland 24 which can then fit snugly around a guide wire or a dilator or the shaft of an artery opening catheter or stent delivery catheter. Furthermore, when the nut 22 is fully screwed onto the threaded base 21, the central lumen of the gland 24 can be totally closed so that no blood will leak out of the guiding catheter's proximal end with no guide wire or catheter placed through that gland 24.

Figure 5:
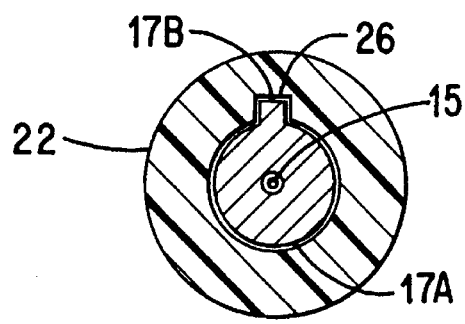
FIG. 5 is an enlarged transverse cross section of the Tuohy-Borst fitting at section 5—5 of FIG. 1.

FIGS. 4 and 5 also show a keyway 26 in the nut 22 which is adapted to mate with the key 17B of the dilator handle 17. This alignment guarantees that the bends in the distal sections of the guiding catheter tube 11 and the dilator 16 oppose each other so as to straighten the guiding catheter system 10 as shown in FIG. 1. In this position, the guiding catheter with dilator 16 in place can be readily advanced over the guide wire 15 until the distal end of the guiding catheter 12 is located near the ostium of the artery (e.g., a coronary artery) to which access is desired. The dilator 16 can then be withdrawn and the guiding catheter 12 will assume its desired distal section shape as shown in FIG. 2. The interventionalist can then place the guiding catheter's distal end 19 into the ostium of that artery.

As shown in FIGS. 1 and 2, the threaded base 21 can include an indicator mark 27 which, when aligned with an indicator mark 28 on the nut 22, informs the operator that the tube 11 and dilator 16 are positioned so that together they form a straight distal end section as shown in FIG. 1. When the nut is rotated 180° away from the position shown in FIGS. 1 and 2, the distal end section of the tube 11 will be as shown in FIG. 2 even when the dilator 16 is placed therein. Between the positions when the indicator marks 27 and 28 are aligned or at 180° from each other, the distal end section of the guiding catheter system 10 will be formed into some intermediate curved shape. Such intermediate shapes may be of value in advancing the distal end of the guiding catheter system 10 through the arterial vasculature.

It is also conceived that a straight dilator without a key could be used with the guiding catheter 12 that is shown in FIG. 2. Such a dilator would tend to straighten the guiding catheter 12. The stiffer the distal section of such a dilator, the straighter would be the distal section of the assembly of the dilator with the guiding catheter 12. Of course, when such a straight (or curved) dilator would be pulled out, the distal section of the guiding catheter 12 would assume its proper shape as generally illustrated in FIG. 2. Furthermore, a dilator with two short stiffened sections (for example using metal bands) which would lie inside the curves 11A and 11b could straighten the guiding catheter's distal section while allowing flexability over the remaining portions of the guiding catheter's distal section.

After the dilator is fully withdrawn and the guiding catheter's distal end is placed into the ostium of an artery, a balloon angioplasty catheter or an atherectomy catheter (i.e., an artery opening catheter ) could be placed through the guiding catheter 12 and a selected stenosis in that artery could be opened to improve blood flow. The artery opening catheter could then be withdrawn, and a stent delivery catheter could be used to place a stent at the site of the opened stenosis. The stent delivery catheter would then be removed and the guiding catheter system 10 could be removed.

If continued access to the artery is desired, the guide wire 15 could remain in place after the guiding catheter system 10 is removed, and an intoducer sheath having the same outside diameter as the guiding catheter tube 11 could be inserted through the skin at the groin and into the femoral artery. Although this would then require the additional component of an intoducer sheath, the procedure would be improved because the hole required to be made through the wall of the femoral artery would be two French sizes smaller. For example, if a 10 French guiding catheter was used, only an 8 French introducer sheath would be required after the guiding catheter is removed since they both have approximately the same outside diameter. If it were initially required to place the guiding catheter 12 through an introducer sheath, a 10 French guiding catheter would require a 10 French introducer sheath which obviously is two French sizes larger in outside diameter as compared to an 8 French sheath that could be used after the guiding catheter is fully withdrawn from the body.

It should also be pointed out that the Tuohy-Borst fitting 20 with side arm 14 precludes the need for using a Tuohy-Borst "Y" adaptor that would normally be joined to the female Luer lock fitting at the proximal end of currently used guiding catheters. The manifold for fluid delivery would be connected to the side arm 14 and the Tuohy-Borst fitting 20 would be used in the manner previously described. A stop cock 30 having a Luer nut 31, side ports 33 and 34 and operating lever 34 (shown in FIG. 4 in the closed position to prevent outflow of blood) could also be placed at the proximal end of side arm 14. Even without the use of a dilator, (i.e., the guiding catheter 12 would be inserted through an introducer sheath) a guiding catheter 12 as shown in FIG. 2 without a dilator would offer an advantage over existing guiding catheters in that a Tuohy-Borst "Y" adaptor would not be required.

Thus the objectives of using a guiding catheter without passing it through an intoducer sheath and the elimination of the need for a separate Tuohy-Borst "Y" adaptor have been shown. Furthermore, the objective of inserting a guiding catheter over a guide wire without the free release of blood through the guiding catheter's proximal end can be accomplished by compressing the gland 24 around the guide wire as the guiding catheter is advanced through the arterial system.

Figures 6A, 6B:
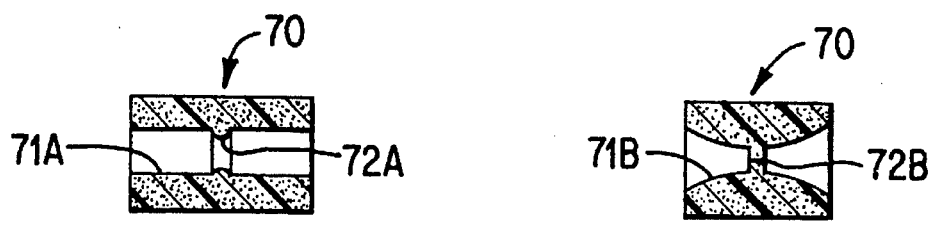
FIG. 6A is a cross section of a Tuohy-Borst gland with a half "O" ring, with the gland shown in a fully open position.
FIG. 6B is a cross section of a Tuohy-Borst gland with a half "O" ring with the gland in a fully closed position.

FIGS. 6A and 6B illustrate an alternative design for the soft elastomer gland of a Tuohy-Borst fitting. Specifically, FIG. 6A shows a gland 70 in its open (not compressed) state. The gland 70 has a generally cylindrical interior surface 71A on which is placed a half "O" ring 72A. When a nut 22 of FIG. 1 is tightened, the gland 70 can be deformed to the shape shown in FIG. 6B wherein a highly curved interior surface 71B is formed with the half "O" ring 72B being distorted to a closed or nearly closed position as shown in FIG. 6B.

This invention envisions that the Tuohy-Borst gland (such as glands 24 or 70) could be fabricated from a soft elastomer such as a low durometer silicone rubber. Furthermore, powdered Teflon or powdered graphite could be incorporated into the soft elastomer to improve its lubricity.

Figure 7:
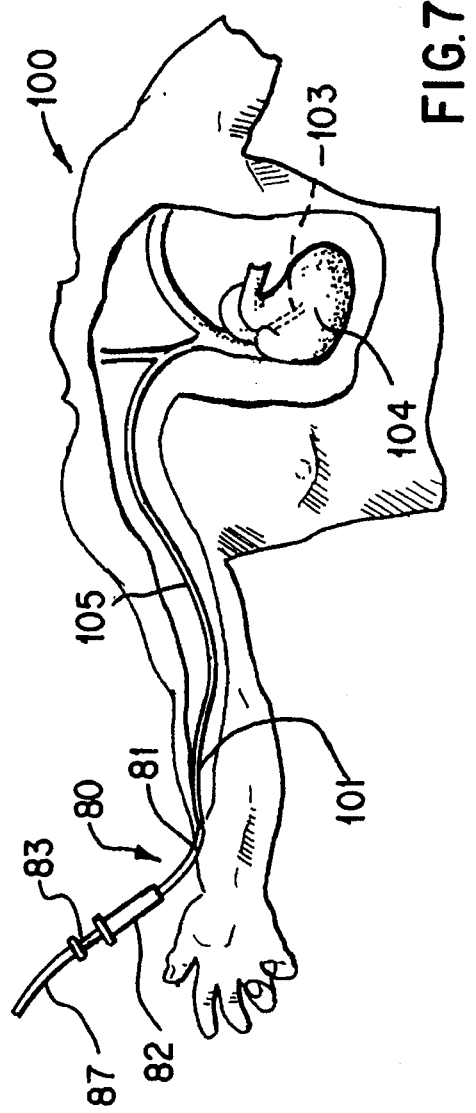
FIG. 7 is a diagram illustrating how the invention would be used to access the coronary artery from the radial artery in the arm.
Figure 8:
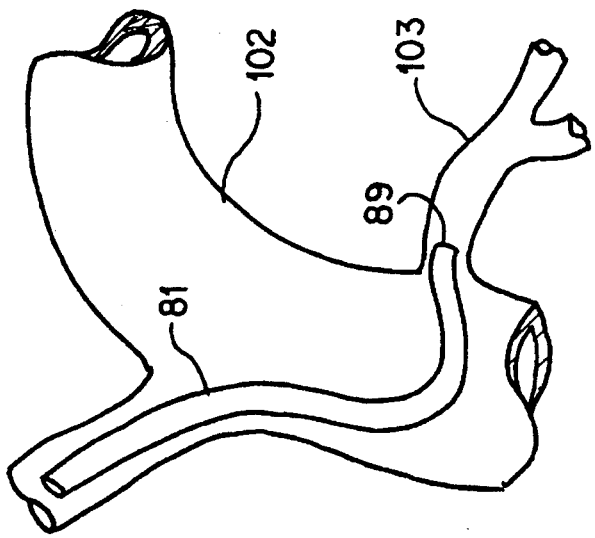
FIG. 8 is a diagram showing how the distal end of the guiding catheter is placed in the ostium of a coronary artery.

FIG. 7 shows the guiding catheter system 80 having an elongated tube 81, a guide wire 85, a female Luer fitting 80, and also showing a handle 87 of a dilator which has an elongated tube that is placed through the central passageway of the tube 81. FIG. 7 does not show any parts of the guiding catheter system 80 that are within the body 100. FIG. 8 shows the guiding catheter tube 81 placed through the radial artery 101 into the aorta 102 with its distal end 89 placed within the ostium of a main coronary artery 103 of the heart 104.

The method for using this guiding catheter system 10 for accessing a coronary artery would be as follows:

(a) A site at the wrist would be prepared in a typical manner including percutaneous insertion of an arterial access needle followed by the insertion of a guide wire 85 through the access needle. (An arterial access needle and method for use are described in detail in U.S. Pat. No. 5,295,969).

(b) The guiding catheter system 80 would be inserted with the dilator advanced over the guide wire 85. The configuration would then be as shown in FIG. 1.

(c) The guiding catheter system 80 would be advanced until its distal end 89 lay in the aorta 102.

(d) The guide wire 85 and the dilator would then be removed.

(e) The elongated tube 81 would then be advanced until its distal end 89 was situated in the ostium of a coronary artery as shown in FIG. 8.

The method of steps (a) through (e) inclusive, allows access to a coronary artery 103, without the use of an introducer sheath. This reduces by 2 French sizes the size of the hole made in the radial artery.

A great advantage in using the radial artery (as opposed to the femoral artery at the groin) is that there is a much lower rate of post-procedure bleeding complications. Thus, the patient can be discharged much sooner thereby providing reduced hospitalization costs.

If it is desired to provide a continuing access to the patient's arterial system after the guiding catheter system 10 is withdrawn, some additional steps involving of the placement of an introducer sheath through the artery at the point where the guiding catheter system 10 enters the arterial system can be performed. In this case, an introducer sheath (such as the sheath described in U.S. Pat. No. 5,180,376) would be of the same outside diameter as the guiding catheter system 80. Thus, the smaller size hole in the artery (as compared to initially placing the guiding catheter system 80 through an introducer sheath having a larger outside diameter) would be maintained.

The extra steps to be accomplished for insertion of an introducer sheath would be as follows:

(f) Remove the guiding catheter system 80 while leaving a guide wire in place through the artery.

(g) Place the proximal end of the guide wire though the central passageway of an introducer sheath dilator that is positioned within an introducer sheath.

(h) Advance the dilator and introducer sheath over the guide wire and into the artery.

(i) Remove the dilator and guide wire leaving the introducer sheath in place for the administration of drugs or for easy access to the patient's arterial system in case a medical emergency develops.

It should be understood that the method described herein is particularly well suited for use in the radial artery. However the method described herein, particularly placing an introducer sheath after the guiding catheter system 80 is removed, can be accomplished at any access site of the human body such as the brachial artery 105 in the arm, (as shown in FIG. 7) the femoral artery at the groin, or the carotid artery in the neck. It should also be understood that the guiding catheter system with a Tuohy-Borst fitting at its proximal end as described herein could also be used for this novel method of arterial access.

Although the discussion herein has been principally concerned with coronary guiding catheter systems, the present invention is well suited for the placement of guiding catheters into the ostia of other arteries such as the carotid and renal arteries as well as coronary artery bypass grafts.

Various other modifications, adaptations, and alternative designs are of course possible in light of the above teachings. Therefore, it should be understood at this time that within the scope of the appended claims, the invention may be practiced otherwise than as specifically described herein.

What is claimed is:

1. A method for accessing human arteries without the use of an introducer sheath, the method comprising the following steps:

(a) percutaneously inserting an arterial access needle through an arterial access site on the skin until the needle point is situated within the artery;

(b) place a guide wire through the access needle and into the arterial lumen;

(c) remove the access needle leaving the guide wire in place;

(d) advance a guiding catheter system over the guide wire and into the arterial lumen, the guiding catheter system comprising;

an elongated hollow tube having a central passageway throughout its entire length and also having proximal and distal ends and a distal section, the hollow tube's distal end being tapered for easy introduction into a blood vessel and the distal section having a bend adapted to facilitate introduction into and retention within the ostium of an artery; and a dilator having an elongated body and having a central passageway throughout its entire length which central passageway is adapted to slide snuggly over a guide wire, the dilator also having proximal and distal ends and a distal section and also having a handle located at the dilator's proximal end, the dilator being tapered at its distal end, the dilator being adapted to slide snuggly through the central passageway of the elongated tube;

(e) remove the dilator and guide wire from the elongated tube;

(f) advance the distal end of the guiding catheter system into the ostium of an artery;

(g) perform an artery opening or angiographic procedure; and (h) remove the guiding catheter system from the patient's arterial system.

2. The method of claim 1 wherein the arterial access site is over the radial artery in the arm.

3. The method of claim 1 wherein the arterial access site is over the brachial artery in the arm.

4. The method of claim 1 wherein the artery into which the guiding catheter system's distal end is placed is a coronary artery.

5. The method of claim 1 wherein the artery into which the guiding catheter system's distal end is placed is a carotid artery.

6. The method of claim 1 wherein the artery into which the guiding catheter system's distal end is placed is a renal artery.

7. The guiding catheter system of claim 1 wherein the entire length of the dilator is straight.

8. The guiding catheter system of claim 1 wherein the distal sections of the elongated hollow tube and the dilator are each curved.

9. The method of claim 1 wherein the guiding catheter system further comprises a Tuohy-Borst fitting integrally attached as a one-piece construction at the hollow tube's proximal end, the Tuohy-Borst fitting including a threaded base, a threaded nut and an elastomer gland that can be tightened around the dilator by screwing the threaded nut onto the threaded base.

10. The method of claim 9 wherein the dilator is placed within the elongated hollow tube to form an essentially straight, tube-dilator assembly when an indicator mark on the threaded base is aligned with an indicator mark on the threaded nut.

11. The method of claim 9 wherein the distal sections of the elongated hollow tube and the dilator are each curved and further, the dilator includes a key at its proximal end that fits into a keyway in the threaded nut of the Tuohy-Borst fitting.

12. The method of claim 9 wherein the Tuohy-Borst fitting has a side arm tube joined to the Tuohy-Borst fitting's threaded base, the side arm tube having distal and proximal ends.

13. The method of claim 12 wherein the side arm tube has a female Luer fitting at its proximal end.

14. The method of claim 12 wherein the side arm tube has a stop cock at its proximal end.

15. The method of claim 9 wherein the gland of the Tuohy-Borst fitting includes a half "O" ring on its interior surface.

16. The method of claim 9 wherein the gland of the Tuohy-Borst fitting is fabricated from a soft elastomer which elastomer includes a powdered Teflon.

17. The method of claim 9 wherein the gland of the Tuohy-Borst fitting is fabricated from a soft elastomer which elastomer includes a powdered graphite.

18. The method of claim 1 including the following additional steps:

(i) retain a guide wire in the artery after the guiding catheter system is removed;

(j) advance together a conventional introducer sheath including an introducer sheath dilator percutaneously through the arterial access site and over the guide wire until most of the length of the introducer sheath lies within the arterial lumen; and (k) remove the guide wire and introducer sheath dilator leaving the introducer sheath placed percutaneously in the aerial lumen.

19. The method of claim 1 wherein at least one distal section near the dilator's distal end is stiffer than the remaining sections of the dilator so as to resist bending at such at least one distal section.

* * * * *